(12) United States Patent
Campbell

(10) Patent No.: US 6,195,806 B1
(45) Date of Patent: Mar. 6, 2001

(54) EAR PROTECTOR

(76) Inventor: Staphea S. Campbell, 1730 Silver Way, Lithia Springs, GA (US) 30122-3956

(*) Notice: Subject to any disclaimer, the term of this patent is extended or adjusted under 35 U.S.C. 154(b) by 0 days.

(21) Appl. No.: 09/306,258

(22) Filed: May 6, 1999

(51) Int. Cl.⁷ ........................................... A42B 1/06
(52) U.S. Cl. ................................ 2/209; 2/209; 128/866
(58) Field of Search ............................... 2/209, 208, 174, 2/423, 455, DIG. 11; 128/864, 866

(56) References Cited

U.S. PATENT DOCUMENTS

| | | | |
|---|---|---|---|
| 4,991,686 | * | 2/1991 | Allen .................................... 181/131 |
| 5,615,417 | * | 4/1997 | Jackson .................................. 2/209 |
| 5,718,001 | * | 2/1998 | Wright ................................... 2/209 |
| 5,920,912 | * | 7/1999 | Patchett ................................. 2/209 |

FOREIGN PATENT DOCUMENTS

| | | | |
|---|---|---|---|
| 813532 | * | 7/1949 | (DE) .................................... 2/209 |
| 686061 | * | 7/1930 | (FR) ..................................... 2/209 |
| 834692 | * | 11/1938 | (FR) ..................................... 2/209 |
| 26402 | * | 12/1905 | (GB) .................................... 2/209 |

* cited by examiner

Primary Examiner—Gloria M. Hale
Assistant Examiner—Tejash Patel
(74) Attorney, Agent, or Firm—Thomas, Kayden, Horstemeyer & Risley

(57) ABSTRACT

The ear protector (10) includes a pair of ear covers (12 and 14) mounted at the ends of a U-shaped yoke (16). Each ear cover includes an arcuate ear engager (32) and a cushion insert (43).

4 Claims, 2 Drawing Sheets

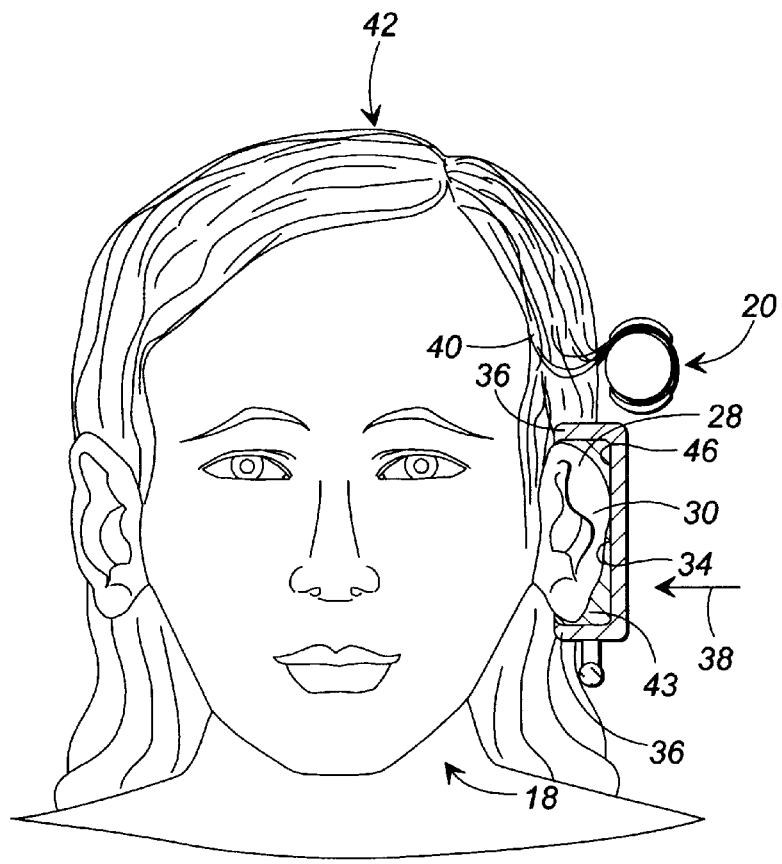
FIG. 2
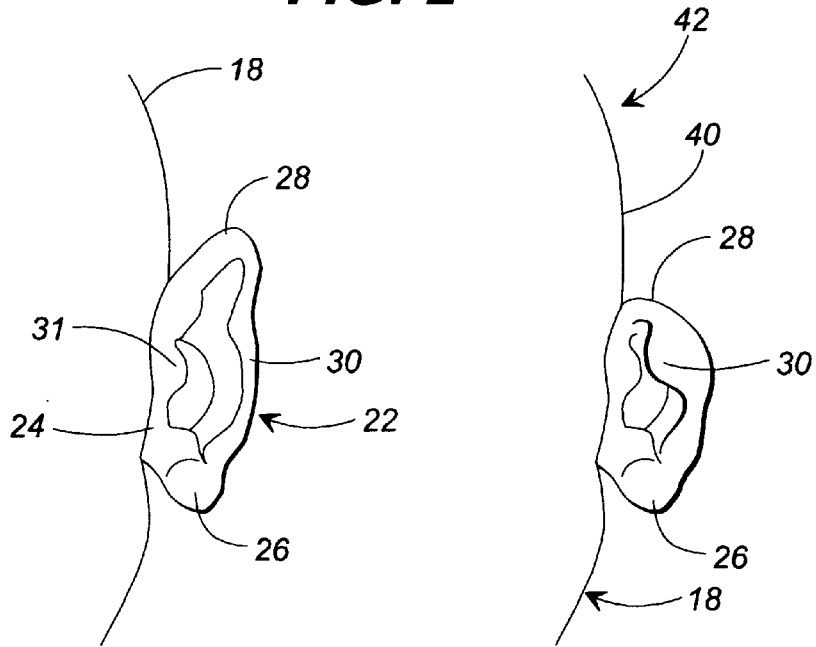
FIG. 3          FIG. 4

EAR PROTECTOR

FIELD OF THE INVENTION

The invention relates to a covering for the ears of the human body, particularly to a pair of protective ear coverings which can be worn about the ears and which can be used to fold the upper ear lobes of the ear away from the scalp while treating the hair of the person about the ears.

BACKGROUND OF THE INVENTION

When a person uses a curling iron or other device about the head for the purpose of curling or otherwise treating the hair of the head, there are times when the device being used is hot and can burn an ear of the person during use. For example, when a curling iron is used adjacent an ear, with the hair being wound about the heated iron, it is difficult for the person to accurately control the position of the curling iron. There are times when through inattention or accident, the curling iron is likely to engage the upper lobe or rear lobe of the ear. This is because it is sometimes desirable to place the curling iron immediately adjacent the ear so as to curl the hair closest to the ear, and because the upper lobe and rear lobe of the ear usually protrude toward the hairline of the head.

U.S. Pat. No. 5,718,001 discloses a protective ear covering device which includes a pair of mutually opposed earmuffs mounted at the ends of a strap, and a drawstring is arranged to be pulled by the wearer so as to progressively close the openings into the earmuffs, thereby closely encircling the earmuffs about the ears. This is for protecting the ears from heat and hair dressing preparations while the hair of the user is being treated. However, the use of a drawstring type protective ear covering device requires the provision of a support strap having a passage therethrough for drawstrings and the threading of the drawstrings through the strap, together with the use of a substantial amount of material in the ear protectors. Also, the user is required to manipulate the drawstring of the ear protector when placing the protector about the ears, and the material of the ear protector is likely to protrude into the space surrounding the ears, forming an obstruction to the curling iron, etc.

SUMMARY OF THE INVENTION

Briefly described, the present invention comprises an ear protector for protecting the ears of a person during the application of heat to the hair of the person. A pair of ear covers are provided, with each cover adapted for mounting against the upper and rear lobes of an ear, with the upper and rear lobes folded over away from the hair line of the person. The ear covers each include an arcuate ear engager and a soft face for engaging the upper and rear lobes of an ear. The soft face material is, for example, a foam rubber or other heat resistant cushion material and is placed in a recess of the relatively hard ear engager, which can be made of plastic. Both the cushion material and the ear engager are made of heat insulation material and the ear covers are sized and shaped to cover the upper and rear lobes of the ears when folded away from the head. A U-shaped support yoke is mounted to the ear covers. The yoke has a pair of arms joined at their lower ends to each other and each arm has at its upper end a fork-shaped support structure that is connected in a supporting relationship to an ear engager of each ear cover. The U-shaped support yoke holds the ear covers in a mutually opposed relationship. The support yoke is of generally U-shaped configuration and spans a space larger than the distance from a person's ears and about the chin of a person, so that the support yoke can hang downwardly from the ears about the chin of a person when the device is being used.

The ear engagers are shaped to maintain the upper and rear lobes of a person's ears in a folded configuration away from the head of the person. Generally, the arcuate ear engagers are shaped approximately like the helix of a typical ear and urge the upper and rear lobes of the ear downwardly away from the scalp of the head, while the heat insulation characteristics of the materials from which the ear engagers are made protect the folded and protruding upper and rear lobes of the ears from contact by a heated curling iron, etc.

Thus, it is an object of the present invention to provide an improved ear protector for protecting the ears of a person during the application of heat to the head and hair of a person.

Another object of the invention is to provide an improved ear protector which includes arcuate ear engagers which are mounted against the upper and rear lobes of a person's ears when folded away from the head, including a support yoke for manipulation by the wearer and for maintaining the ear engagers in mutually spaced relationship and biased toward the ears to snugly hold the ears in the desired out-of-the-way positions when treating the hair adjacent the ears.

Another object of the invention is to provide an improved ear protector for holding the upper and rear lobes of the ears of a person away from the scalp while heat is applied to the hair about the ears.

Other objects, features and advantages of the present invention will become apparent upon reading the following specification, when taken in conjunction with the accompanying drawings.

BRIEF DESCRIPTION OF THE DRAWINGS

FIG. 2 is a front cross-sectional view of one of the ear engagers and its cushion insert of the ear cover of FIG. 1, with the opposite ear cover, not shown but being a mirror image thereof.

FIG. 3 is a front silhouette of a person's ear in its natural, unfolded shape.

FIG. 4 is a front silhouette of a person's ear, similar to FIG. 3 but showing the ear when folded over.

DETAILED DESCRIPTION

Figure 1:
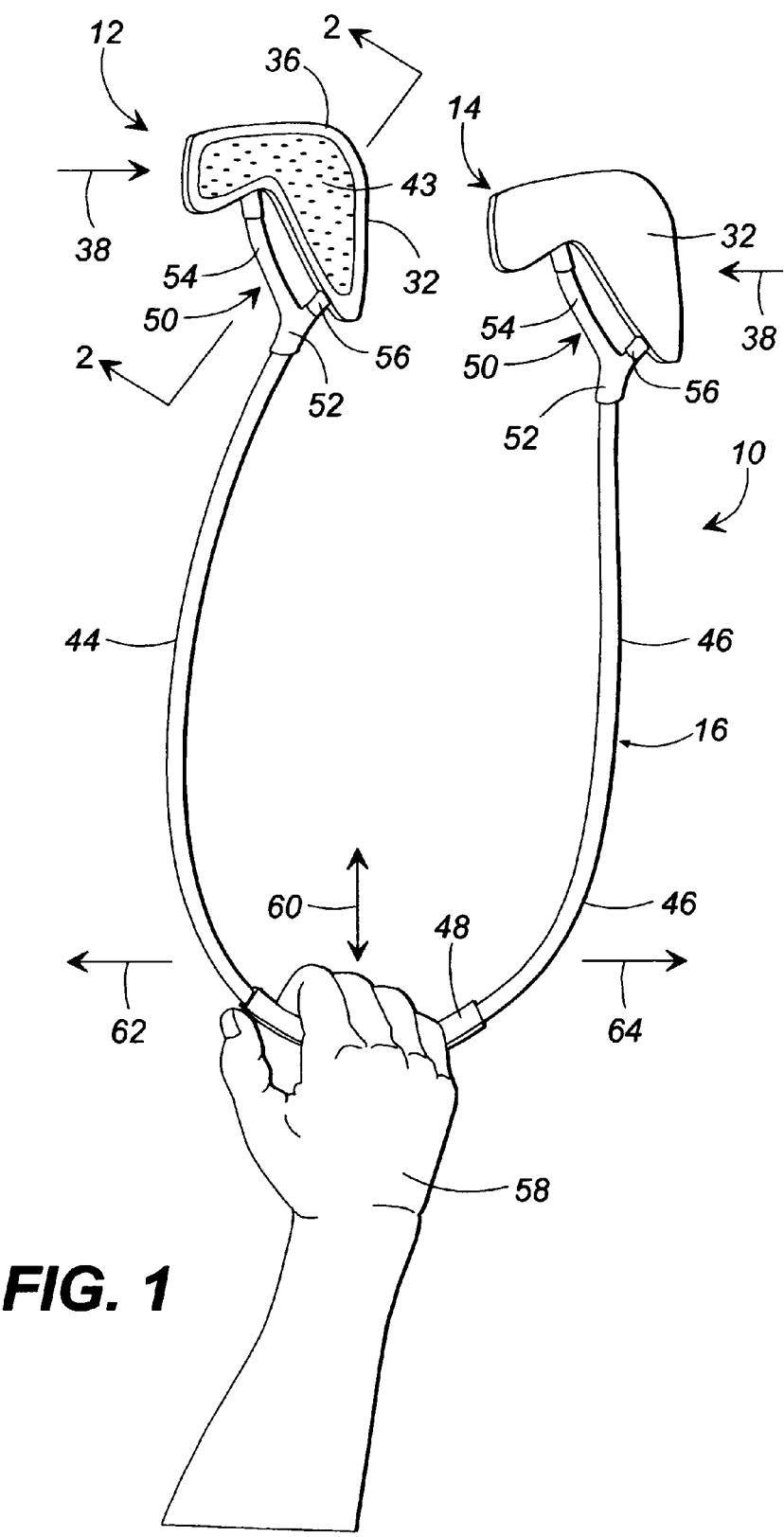
FIG. 1 is a perspective illustration of the ear protector.

Referring now in more detail to the drawings, in which like numerals indicate like arts throughout the several views, FIG. 1 discloses an ear protector 10 which includes a pair of ear covers 12 and 14 mounted on the ends of a support yoke 16. The support yoke supports the ear covers 12 and 14 in a mutually opposed relationship.

As illustrated in FIG. 2, the ear protector 10 is to be mounted with its ear covers 12 and 14 positioned against the folded ears of the head of a person 18, and the support yoke 16 is allowed to extend downwardly under the influence of its own weight beneath the chin of the person, with the support yoke supported by the ear covers 12 and 14. Generally, the ear protector will protect the ears of the person during the use of a heated implement, such as a curling iron 20.

As illustrated in FIGS. 3 and 4, a person's ear 22 includes a base 24 adjacent the head 18 of the person, a lower lobe 26 and a helix which includes an upper lobe 28, and a rear lobe 30, and a central portion 31.

Each ear cover 12 and 14 includes an arcuate ear engager 32 which is to be applied about the ear, against the folded rear and/or upper lobes 28 and 30.

The arcuate ear engagers 32 each include a recessed inner surface 34 (FIG. 2) which is arranged to be urged toward the upper and rear lobes 28 and 30 of the folded ear, generally in the direction indicated by arrows 38, for the purpose of maintaining the folds of the upper and rear lobes 28 and 30 away from the scalp 40 of head 42 of the wearer 18. The recessed inner surface 34 is bounded by a perimeter flange 36. A cushion insert 43 is positioned in the recess 34 and is maintained in position by the perimeter flange and adhesive 46 positioned between the cushion insert and the recessed surface 34. The cushion insert is softer than its arcuate ear engager 32 and usually engages against the upper and/or rear lobes 28 and 30 of a folded ear, to comfortably hold the lobes folded away from the scalp 40. It is anticipated that the cushion insert, preferably to be made of sponge rubber or plastic, will yield against the force applied to it by the ear protector to the ear, causing a slight recess or indentation in the cushion insert that conforms to the engaged surfaces of the ear. This recess as well as the perimeter flange tend to hold the arcuate ear engager and the cushion insert in place on the ear when biased laterally against the ear as shown by arrows 38.

Although the cushion insert is illustrated as being substantially flat, it can be formed in other shapes, such as a concave shape that faces the ear.

Support yoke 16 is approximately U-shaped and includes side legs 44 and 46 extending upwardly from a curved base portion 48, with the side legs being connected at their upper distal ends to the ear covers 12 and 14. A forked mounting bracket 50 is molded directly to each ear cover 12 and 14, and includes a mounting stem 52 telescopically mounted on the distal end of a side leg 44 or 46 of the support yoke 16 and forked tines 54 and 56 which are rigidly connected to an ear engager 32.

The support yoke 16 is formed of spring material, such as spring steel or plastic to a predetermined shape that places the ear covers 12 and 14 in a close mutually opposed relationship, less than the usual thickness of the wearer's head, so that when the ear covers are moved apart the support yoke biases the ear covers toward engagement with the ears of the wearer, as illustrated by arrows 38. This assures that enough frictional contact will be made between the ear covers and the folded over ears of the wearer to hold the ear protector in place without requiring additional support by the wearer.

As illustrated in FIG. 1, the wearer of the device mounts the ear covers 12 and 14 about the ears, with the support yoke 16 extending under the influence of its own weight beneath the chin of the wearer. The wearer may use his or her hand 58 to manipulate the support yoke 16, generally as indicated by arrows 60, 62 and 64. When one of the ear covers 12 or 14 is moved downwardly by the hand 58, the arcuate ear engager 32 of that ear protector will tend to fold the upper and/or rear lobes 28 and 30 of the ear away from the scalp of the person 18. In addition, the hard surface heat insulation material of the ear engagers 32 protects the ear from engagement by the curling iron 20, or other heat application instrument.

In most instances, once the ear protector is mounted as illustrated in FIG. 2, the biasing of the ear covers together by the support yoke 16 and the weight of the device tends to hold the ear covers in engagement with the folded ears, as illustrated in FIG. 2.

In some instances, the user of the ear protector 10 will manipulate the support yoke 16 with a hand 58 so as to pull downwardly and forwardly on one or both ears to make sure that the ear is in a protected position.

When a curling iron 20 is being used above the ear, the wearer typically will urge the ear cover adjacent the curling iron downwardly, and when the curling iron is being used behind the ear, the wearer typically would urge the ear cover forwardly, so as to fold the upper and/or rear lobes of the ear in a direction away from the curling iron. In either situation, the force applied by the ear covers against the ears from the support yoke usually will be enough to hold the ears in their folded shapes.

The support yoke 16 is made of a springy material that is formed so as to urge the mutually opposed ear covers 12, 14 toward each other. This results in the ear covers being urged by the spring of the support yoke toward the ears. With this arrangement, the arcuate ear engagers 32 will become mounted against and about the ears, so that the entire ear protector is supported by the opposed ears of the wearer 18. In most instances, the inward force of the ear protector will tend to urge the upper lobe 28 of each ear away from the head, without requiring the wearer to use his or her hand 58. The ear protector usually functions to protect the ears of the person in a hands-free situation, leaving both hands available for manipulating the curling iron or other implement.

Although a preferred embodiment of the invention has been disclosed in detail herein, it will be obvious to those skilled in the art that variations and modifications of the disclosed embodiment can be made without departing from the spirit and scope of the invention as set forth in the following claims.

What is claimed is:

1. An ear protector for protecting the ears of a person during the application of heat to the head of the person, comprising:

a pair of ear covers, each ear cover adapted for mounting against the upper and rear lobes of an ear when the upper and rear lobes of the ear are folded away from the scalp of the person;

each ear cover including an arcuate ear engager for urging upper and rear lobes of an ear folded toward the middle of the ear;

each of said ear covers including cushion material arranged to engage the folded-over upper and rear lobes of an ear when said ear cover extends about an ear;

a U-shaped support yoke having a pair of arms, each arm connected in a supporting relationship to one of said ear covers and holding said ear covers in mutually opposed relationship about the ears of a person's head, said support yoke being larger than the distance from one ear, around the chin area and to the other ear of a person for hanging from the ears about the chin of a person;

said U-shaped support yoke being made of a springy material adapted to urge said pair of ear covers toward each other for urging said ear covers toward the person's head against the ears of the person so that said ear protector is supported by the ears of the person;

said ear covers being shaped to fold the upper and rear lobes of the ears of a person's head away from the head.

2. The ear protector of claim 1, and wherein said ear covers include cushion material for directly engaging an upper ear lobe when folded over the central portion of an ear.

3. The ear protector of claim 1, wherein said support yoke comprises a leaf spring.

4. The ear protector of claim 1, wherein said arcuate ear engagers are formed into an arcuate shape, and each of said distal ends of said arms of said support yoke being connected to one of said arcuate shapes.

* * * * *